United States Patent [19]
Speck

[11] Patent Number: 5,144,247
[45] Date of Patent: Sep. 1, 1992

[54] METHOD AND APPARATUS FOR REDUCING IR ERROR IN CATHODIC PROTECTION MEASUREMENTS

[75] Inventor: Robert M. Speck, Richmond, Tex.

[73] Assignee: Westinghouse Electric Corp., Pittsburgh, Pa.

[21] Appl. No.: 655,881

[22] Filed: Feb. 14, 1991

[51] Int. Cl.⁵ .................................................. G01N 27/42
[52] U.S. Cl. ................................... 324/425; 204/404; 324/71.1; 324/446
[58] Field of Search ............... 324/425, 446, 448, 449, 324/450, 71.2, 713, 715, 724, 71.1; 204/404, 153.1

[56] References Cited

U.S. PATENT DOCUMENTS

| | | | |
|---|---|---|---|
| 2,803,797 | 8/1957 | Cowles | 324/425 |
| 3,763,007 | 10/1973 | Seyl | 324/71.2 |
| 3,766,042 | 10/1973 | Wilson | 324/71.2 |
| 4,137,495 | 1/1979 | Brown | 324/450 |
| 4,219,807 | 8/1980 | Speck et al. | 324/72 |
| 4,305,039 | 12/1981 | Steuernagel et al. | 324/425 |
| 4,332,658 | 6/1982 | Tsuboshima | 324/425 |
| 4,481,474 | 11/1984 | Gerrit | 324/425 |
| 4,591,792 | 5/1986 | Birchmeier et al. | 324/71.1 |
| 4,772,851 | 9/1988 | Schattschneider | 324/71.2 |
| 4,806,850 | 2/1989 | Saumade et al. | |
| 4,902,981 | 2/1990 | Gard et al. | 324/715 |
| 4,940,944 | 7/1990 | Steele et al. | |

FOREIGN PATENT DOCUMENTS

| | | | |
|---|---|---|---|
| 2359413 | 3/1978 | France | 324/71.2 |
| 149011 | 11/1979 | Japan | 324/425 |
| 2023846 | 1/1980 | United Kingdom | 324/449 |

Primary Examiner—Kenneth A. Wieder
Assistant Examiner—Maura K. Regan
Attorney, Agent, or Firm—R. P. Lenart

[57] ABSTRACT

An apparatus for measuring cathodic protection voltage levels on a concealed conductive structure, includes a probe having a standard half cell reference electrode, a working electrode and an auxiliary electrode mounted in a fixed spacial relationship to each other, wherein the reference electrode, working electrode and auxiliary electrode are each in contact with an electrolytic solution. A voltage measuring device is provided for receiving a voltage from said reference electrode. The voltage measuring device provides an indication of the voltage difference between the reference electrode and a common reference point. A switch is included for connecting and disconnecting the working electrode with the common reference point. A voltage detecting circuit detects voltage between the concealed conductive structure, which is subject to a cathodic protection voltage, and the common reference point. A bias voltage is applied to the auxiliary electrode in response to the voltage level between the concealed conductive structure and the common reference point. The voltage measured by the voltage measuring device provides an indication of the adequacy of cathodic protection voltage levels on the concealed conductive structure.

11 Claims, 6 Drawing Sheets

METHOD AND APPARATUS FOR REDUCING IR ERROR IN CATHODIC PROTECTION MEASUREMENTS

BACKGROUND OF THE INVENTION

This invention relates to instruments for measuring cathodic protection voltage levels and to the method used by such instruments to measure cathodic protection voltages.

Cathodic protection of metallic structures immersed in an electrolyte is a well established technique for reducing the rate of corrosion of the structure. An electric current is made to flow from the electrolyte to the structure and the efficacy of the protection is proportional to the current density at the surface of the structure. The protected surface is called the cathode and the surface from which the current flows into the electrolyte is called the anode. Cathodic protection is achieved at the cost of energy used to force the cathodic current to flow from the anode to the cathode through the electrolyte. Energy sources used to provide the cathodic current may take the form of sacrificial anodes or line powered AC to DC rectifiers. Distributing this current over the surface of the structure in a uniform manner to provide ample protection is an objective in the design and installation phase of any cathodic protection system.

Once installed, an indication of the adequacy of protection resulting from the operation of the cathodic protection system may be made by measuring the potential between the structure and the electrolyte. For each combination of metal and electrolyte, there is a potential that is deemed sufficient to ensure that no corrosion will occur. It is the determination of the true electric potential between the metal and the electrolyte with no errors or offsets that has proven to be a difficult task. Often, for structures buried in the earth, it is not feasible to expose the structure to make potential measurements. Measurements made some distance removed from the structure have been accepted as equivalent to the desired close measurements. The electrolyte in which the structure is immersed may be comprised of nearly dry earth to nearly all water and may vary from location to location and with climatic changes at a given location.

If a voltmeter is connected between the test point and a standard copper sulfate half cell situated on the surface of the earth directly above the pipeline, a voltage comprised of two components will be measured. The first component is the desired potential at the surface of the pipeline. The second is the voltage arising as some component of the cathodic protection current flows in the electrolyte in the earth. For a newly installed pipe which has not been subjected to cathodic protection, the potential at the surface of the pipe may be measured to be about 0.45 volts, depending upon the composition of the soil, the pipe, and the electrolyte in which they are immersed. After some months of cathodic current flow, the potential at the surface of the pipe may rise to about 0.80 volts as read on a voltmeter with the cathodic current temporarily interrupted to facilitate the measurement. The value of the soil resistance is unknown and variable with the season, soil conditions, and distance between the test point and the location of the half cell. In addition, the magnitude of the current component which flows through the soil is unknown and variable. As expected, the resulting IR drop cannot be anticipated. These IR voltages commonly exceed several volts and tens of volts in rare situations.

Although a copper sulfate half cell electrode has been most commonly used to ensure that a reproducible and stable contact might be made to the electrolyte during voltage measurements, other stable electrodes may serve equally as well. To further ensure cell accuracy, the current drawn by the measuring device through the internal resistances of the half cell should be minimized.

None of the many techniques for measuring the electrolyte potential, or what is sometimes called the IR drop free potential of a cathodically protected structure, has satisfied all the requirements of accuracy, simplicity and reliability., Most techniques rely upon the fact that the cathodic current is typically pulsating rather than constant. Some techniques even cause the interrupting of the cathodic current flow to create a pulsating current. There is a need for an instrument for measuring cathodic protection voltage levels which uses a simple voltage measuring probe that minimizes the effects of IR voltage drops.

SUMMARY OF THE INVENTION

An apparatus for measuring cathodic protection voltage levels on a concealed conductive structure, constructed in accordance with this invention includes a probe having a standard half cell reference electrode, a working electrode and an auxiliary electrode mounted in a fixed spacial relationship to each other, wherein the reference electrode, working electrode and auxiliary electrode are each in contact with an electrolytic solution. A voltage measuring device is provided for receiving a voltage from said reference electrode. The voltage measuring device provides an indication of the voltage difference between the reference electrode and a common reference point. A switch is included for connecting and disconnecting the working electrode with the common reference point.

A voltage detecting circuit detects voltage between the concealed conductive structure, which is subject to a cathodic protection voltage, and the common reference point. A bias voltage is applied to the auxiliary electrode in response to the voltage level between the concealed conductive structure and the common reference point. The voltage measured by the voltage measuring device provides an indication of the adequacy of cathodic protection voltage levels on the concealed conductive structure.

In an alternative embodiment, an apparatus for measuring cathodic protection voltage levels on a concealed conductive structure, comprises a probe including a standard half cell reference electrode and a metallic electrode mounted in a fixed spacial relationship to each other and separated by an electrolytic solution. A voltage measuring device having a first input terminal for receiving a voltage from the reference electrode and a second input terminal for connection to a concealed conductive structure which is subject to a cathodic protection voltage, detects various voltages in the system. A voltage divider is electrically connected between the reference electrode and the metallic electrode, wherein the voltage divider includes the series connection of first and second resistors. A switching device is provided for connecting the reference electrode to the second terminal while disconnecting the metallic electrode from the first input terminal, or alternatively, connecting the second terminal to a junction point between the first and second resistors while connecting the metallic electrode to the first input terminal.

This invention encompasses both the above apparatus as well as the methods of measurement of cathodic protection voltage levels performed by those apparatus.

BRIEF DESCRIPTION OF THE DRAWINGS

The invention will become more readily apparent to those skilled in the art through the following description of the preferred embodiments, as illustrated in the drawings, wherein:

FIG. 2 is a block diagram of an apparatus for measuring cathodic protection voltage levels, constructed in accordance with this invention;

DESCRIPTION OF THE PREFERRED EMBODIMENTS

Figure 1:
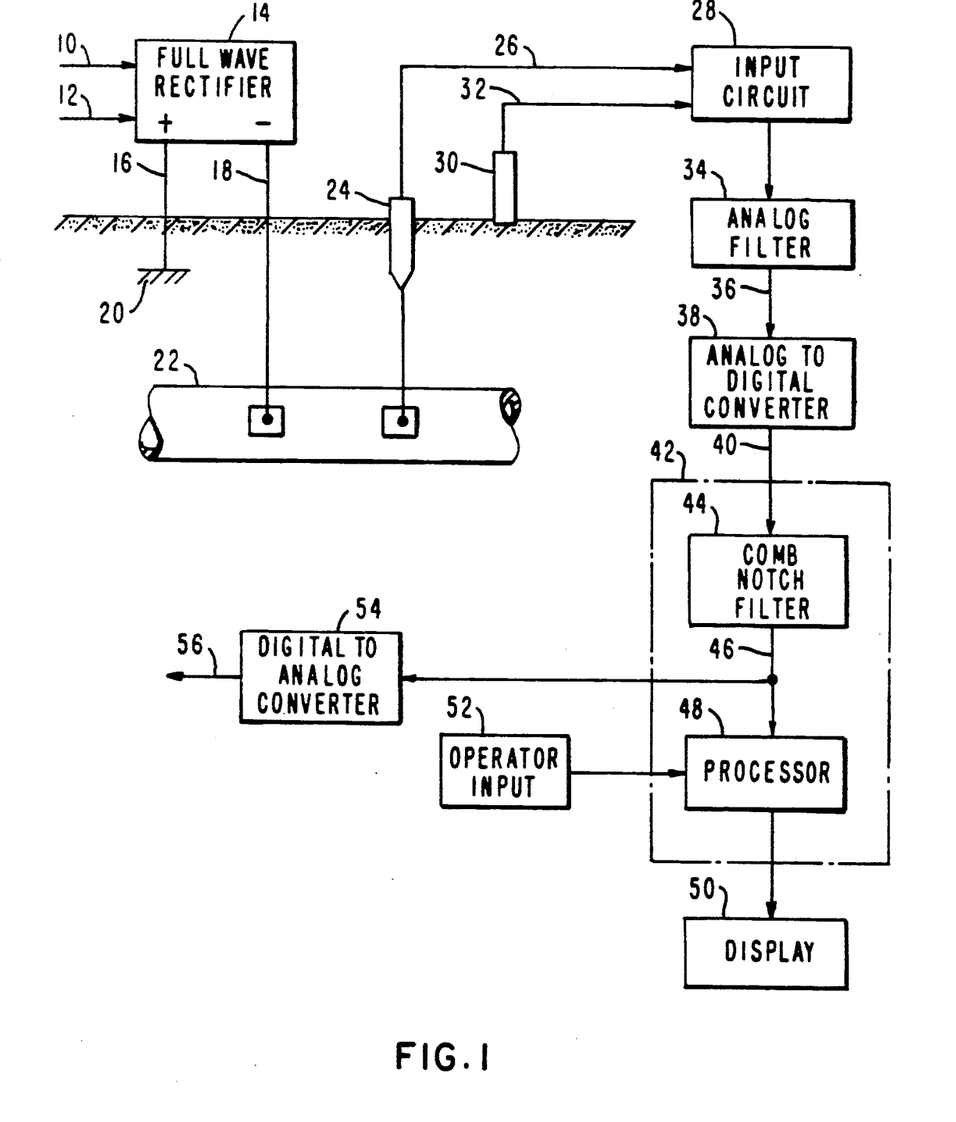

Referring to the drawings, FIG. 1 is a block diagram of a cathodic protection system having a voltage level measuring device constructed in accordance with this invention. In active cathodic protection systems, commercial line power at a nominal 60 Hz frequency in this example, is supplied on lines 10 and 12. A full wave rectifier 14 converts this input to a 120 Hz pulsating DC output on lines 16 and 18. Line 16 is connected to an anodic ground bed 20 constructed in accordance with known techniques. The negative line 18 is connected to an underground pipeline 22. A test point 24, which may be one of many periodically spaced along the pipeline, is provided for making an electrical connection, by way of line 26, between the pipeline and an input circuit 28 in the measuring device. A voltage detecting probe 30 is placed in contact with the ground and is connected to the input circuit via cable 32. In this manner, the input circuit receives voltage signals which are representative of the externally applied full wave rectified power line frequency cathodic protection potential.

Since the voltages may be subject to electrical interference, a 60 Hz analog filter is used to remove the majority of the fundamental power line frequency noise component from the cathodic protection signal which is produced by the input circuit. The resulting filtered analog signal on line 36 is converted to digital form by analog to digital converter 38. This results in a first digital signal on line 40 which is fed to a microcomputer 42. The microcomputer includes a comb notch filter which removes the remainder of the fundamental power line frequency component and, odd harmonics thereof, from the first digital signal thereby producing a filtered digital signal on line 46. This filtered digital signal is fed to the processor 48 of the microcomputer which measures a selected parameter of the filtered digital signal to produce an indication of the adequacy of the cathodic protection potential. This indication is then delivered to a display device 50. Selection of the particular parameter of interest can be made by an operator using an input device 52. A digital to analog converter 54 receives the filtered digital signal on line 46 to produce an analog signal on line 56 that is representative of the original received cathodic protection signal with the fundamental power line frequency component and odd harmonics thereof removed. Additional details of the operation of this system are provided in U.S. Pat. No. 4,940,944, issued Jul. 10, 1990, and hereby incorporated by reference.

Figure 2:
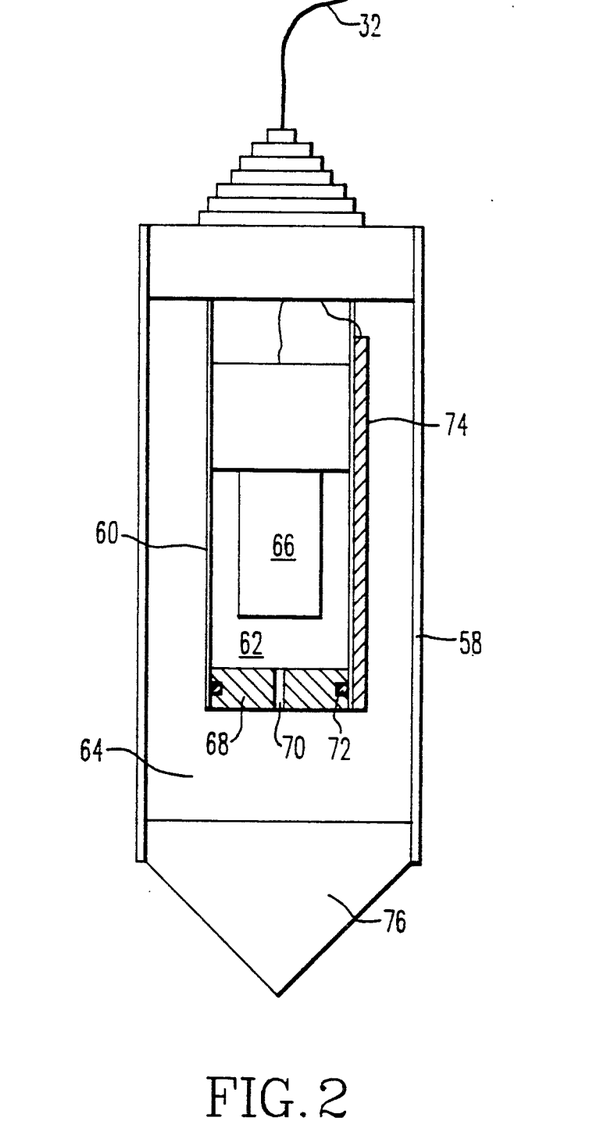
FIG. 2 is side view, partially in cross section, of the probe in the apparatus of FIG. 1.

FIG. 2 is a side view of the probe used in the measuring apparatus of FIG. 1. The probe includes a generally cylindrical outer tube 58 and a generally cylindrical inner tube 60 mounted concentric with each other. Tubes 58 and 60 are comprised of an electrically insulating material. The interior space 62 of tube 60 and the space 64 between tubes 58 and 60 are filled with an electrolytic solution, such as a solution of potassium chloride (KCl). A silver-silver chloride (Ag-AgCl$_2$) half cell reference electrode 66 is mounted within tube 60. A metallic coupon or working electrode 68 is positioned at one end of tube 60. The working electrode 68 includes a central Luggin capillary opening 70 and a peripheral grove for holding an O-ring 72 which seals the edge of the working electrode, such that the electrolyte only passes between spaces 62 and 64 through the capillary opening. An auxiliary electrode 74 is mounted on the outside of tube 60. Electrical connections to the reference electrode, working electrode and auxiliary electrode are provided through cable 32. One end of tube 58 houses a porous ceramic plug 76 which is used to make physical and electrical contact with the ground during measurement of the cathodic protection voltage level.

Figure 3:
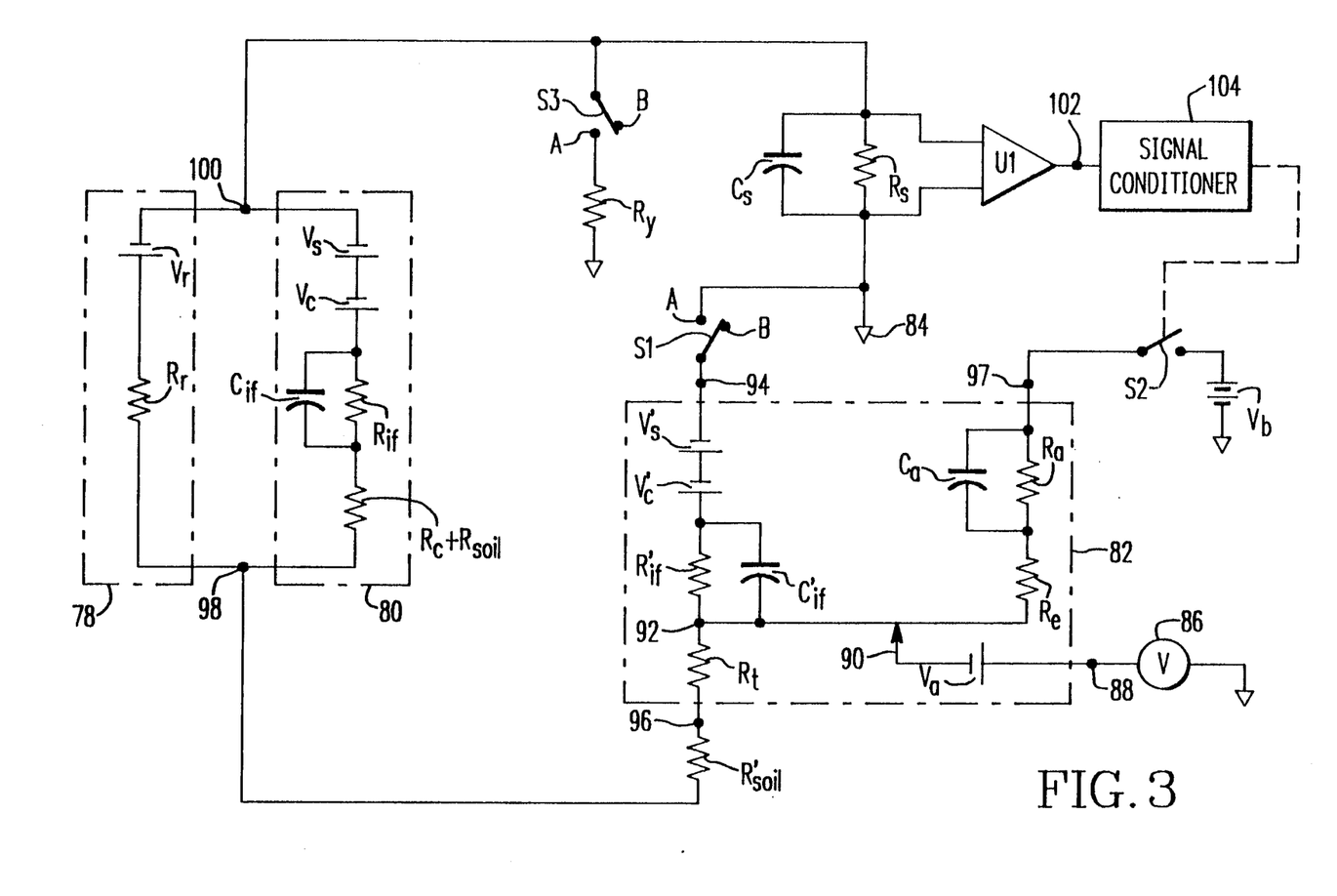
FIG. 3 is a simplified schematic diagram of the input circuit and the probe used in FIG. 1.

FIG. 3 is a simplified schematic diagram of the probe and input circuit used in the measuring device of FIG. 1. Block 78 represents a cathodic protection voltage source having a voltage $V_r$ and a resistance $R_r$. Block 80 represents a concealed conductive structure, such as an underground pipeline, having a standard electrode potential $V_s$, a structure to electrolyte interface concentration potential $V_c$, an interface resistance $R_{if}$, an interface capacitance $C_{if}$, and a coating resistance $R_c$. Resistance $R_{soil}$ is the soil resistance. Block 82 is an equivalent circuit for the probe of FIG. 2. In that block, $V'_s$, $V'_c$, and $V_1$ represent the open circuit voltages produced at the working electrode, the reference electrode, and the auxiliary electrode respectively; $R'_{if}$ and $C'_{if}$ represent the resistance and capacitance of the interface between the working electrode and the electrolyte; $R_a$ and $C_a$ represent the resistance and capacitance of the interface between the auxiliary electrode and the electrolyte; $R_e$ represents the resistance of the potassium chloride electrolyte; and $R_t$ represents the resistance of the probe tip. $R'_{soil}$ corresponds to the soil resistance.

The coupon or working electrode has electrical characteristics similar to that of the concealed structure. The working electrode can be connected or removed from the reference probe aperture by a switch S1 connected between the working electrode and a common point 84 in the circuit. When switch S1 is in position A, the working electrode is connected in the measurement system, and an interface voltage will be accumulated on the working electrode and will be measured by the voltmeter 86 attached between the silver chloride reference cell terminal 88 and the circuit common point. The reference cell sees the interface voltage of the working electrode IR free via the Luggin capillary 90 through an insulated aperture at the center of the working electrode. Node 92 represents the surface of the working electrode where the interface or polarization voltage is sensed.

With switch S1 in the IR free position, A, and switch S2 open, current can flow between nodes 94 and 96 through the ceramic tip of the probe, $R_t$, and the working electrode represented by $R'_{if}$, $V'_c$, and $V'_s$. If switch S2 is closed, current will flow from node 97, charging the interface of the working electrode, $C'_{if}$, via the current return path through node 94. Also, current will flow from node 97 through the probe tip to node 96, and the structure nodes 98 and 100, and back through sensing resistor $R_s$ to complete its path to node 94. The auxiliary electrode current equals the working electrode current plus the current through the probe tip. If switch S1 is in position B, and switch S2 is open, the probe and meter circuitry will become a normal reference cell and the meter 86 will measure the voltage across nodes 98 and 100 of the structure, including the IR drop across the soil and coating resistance.

If switch S3 is in position A, and S1 is in position A, the closure sensitivity of switch S2 will be greatly reduced, in most cases inhibiting S2 from closing. The probe's working electrode will be charged from the potential appearing across nodes 98 and 100. The voltmeter will measure the working electrode voltage, not the IR drop across $R_{soil}$ and $R_t$. If the resistance ratio in the probe path $R'_{if}(R'_{soil}+R_t)$ equals the resistance ratio $R_{if}(R_{soil}+R_c)$ in the structure path, the voltmeter 86 will measure the polarized potential of the structure since the voltage-current characteristics of the working electrode are the same as those of the structure.

If the resistance of resistor $R_y$ is set to yield a polarized voltage reading to correlate closely to a bare structure polarized voltage, in a tap water electrolyte environment ($R_c$ of the structure equals zero), when switch S3 is closed and switch S1 is in position A, the instrument is set for high field gradients such as those found on bare structures. For the measurement of a coated structure, the initial conditions are that switch S3 is open, S1 is in position A, and the voltage across nodes 98 and 100 is greater than the voltage across nodes 94 and 96. At that time, current from node 98 will flow through nodes 96, 92 and 94 back through $R_s$ to node 100. This will develop a negative potential across the inputs of operational amplifier U1 causing a switching signal output at node 102 to be fed to a signal conditioner 104, which delays the signal, stores a charge, and actuates switch S2. Current from the auxiliary electrode, through node 97, flows through the working electrode and back through the structure, thereby recharging capacitor $C_s$ across $R_s$ in the opposite sense. This causes the output of U1 to reverse polarity, causing S2 to open. At this time the current between nodes 96 and 98 is zero and a charging of $C_s$ starts again repeating the cycle. The voltage at the working electrode cycles above and below the true potential of a typical coated structure averaging to the polarized potential.

Figure 4:
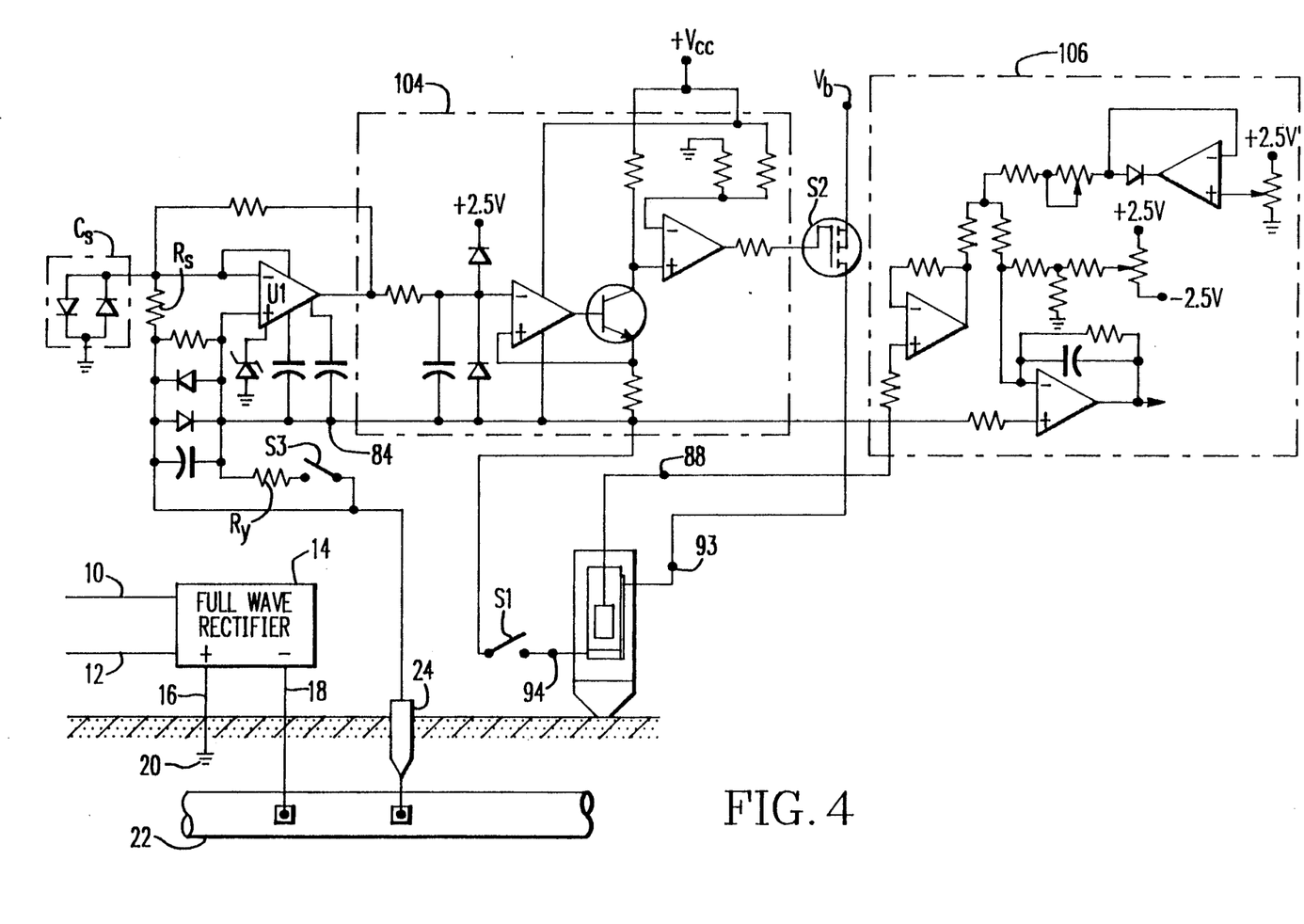
FIG. 4 is a more detailed schematic diagram of the input circuit of FIG. 3.

FIG. 4 is a more detailed schematic diagram of the circuit of FIG. 3. Common elements in FIGS. 3 and 4 have been assigned identical identifiers. Block 106 is the input circuitry to the voltmeter. In the preferred embodiment, the voltmeter is replaced by the indicating circuitry of the instrument shown in U.S. Pat. No. 4,940,944, previously incorporated by reference.

Figure 5:
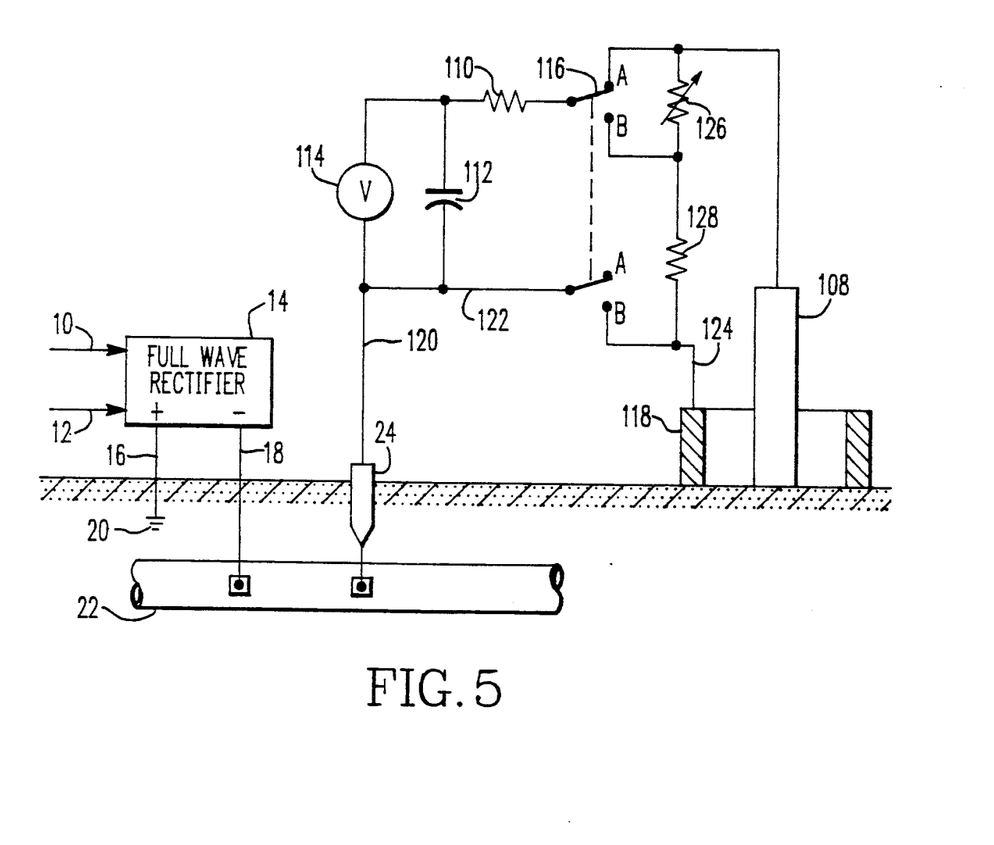
FIG. 5 is a schematic diagram of an alternative embodiment of the invention.

FIG. 5 is a schematic diagram of an alternative embodiment of the invention. In this embodiment, probe 38' includes an industry standard copper sulfate half cell 108 to provide contact with the earth. Resistor 110 and capacitor 112 form a low pass filter which prevents high frequency components of the half cell voltage from entering the voltmeter 114. For low frequency components of the half cell voltage, the filter has little influence. Switch 116 is a double pole double throw type which when in position A allows for selection of normal connection between voltmeter 114 and half cell 108. Voltmeter 114 will operate and indicate as it would have without the addition of resistor 110, capacitor 112, and switch 116.

A metallic thin walled ring 118 shown in cross section is constrained by insulating means, not shown, to be concentric and coplanar with the active end of half cell 108. The exact composition of the metal ring 118 should ideally be the same as the composition of the concealed pipe 22. For that special case, the electropotential generated by the copper sulfate half cell reaction with the pipe is identical to the electropotential generated in the copper sulfate half cell reaction with the metal ring. When switch 116 is switched to position B to connect the pipe through leads 120, 122, and 124 to the ring, electropotentially, the ring is then an extension of the pipe and does not alter the voltage read on the voltmeter. Since it is impractical to match the electropotentials of the pipe and the ring for each situation, an alloy with a slightly higher electropotential than that of the pipe is used for the ring. Variable resistor 126 and fixed resistor 128 allow for the manual adjustment of the shielded half cell to obtain a match with the electropotential of the pipe. Switch 116 permits standard copper sulfate operation when in position A and shielded copper sulfate operation when in position B.

Figure 6:
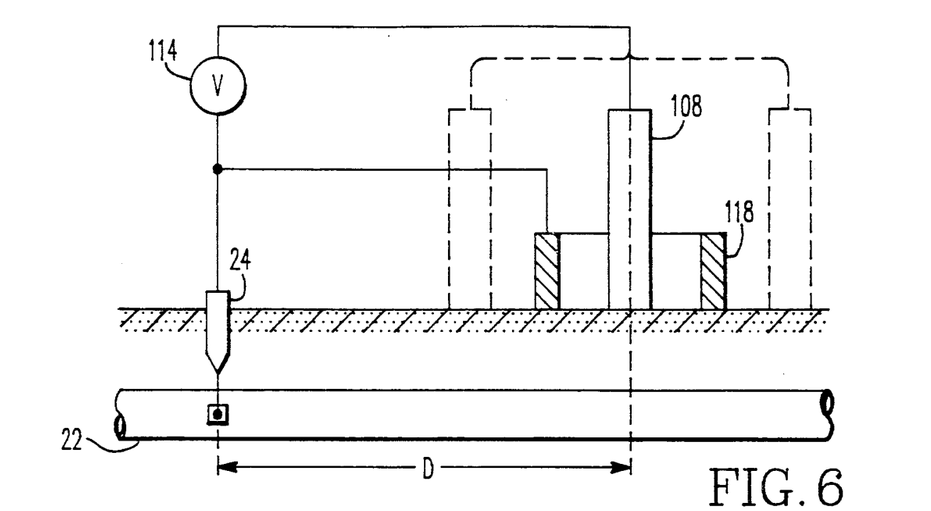
FIG. 6 is a schematic diagram used to illustrate the operation of the device of FIG. 5.

FIG. 6 is a schematic diagram which will be used to illustrate the operation of the device of FIG. 5. For the purposes of this illustration, the copper sulfate half cell may be positioned along the surface of the earth at some distance D from the location of the test point 24, while the ring remains in the position shown. Example alternate positions of the half cell 108 are shown as phantom views.

Figure 7:
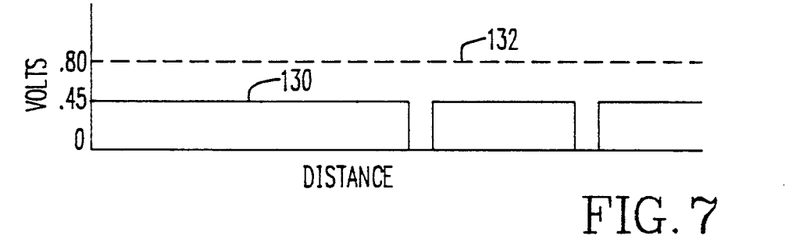
FIGS. 7, 8 and 9 are voltage plots which indicate the voltages in the circuit of FIG. 6.

FIG. 7 shows the voltage which would be read on the voltmeter as the copper sulfate half cell is moved along the surface of the earth, for the case where no cathodic protection current has flowed and the ring is electropotentially the same as the pipe. As illustrated by curve 130, the measured voltage is about 0.45 volts and is independent of the location of the half cell, as long as it does not contact the ring. This constancy of half cell voltage is the basis for potential measurements along the pipe. Cathodic protection will only be achieved, however, by increasing the potential of the pipe to approximately the 0.80 volt level shown by the dotted horizontal line 132.

Figure 8:
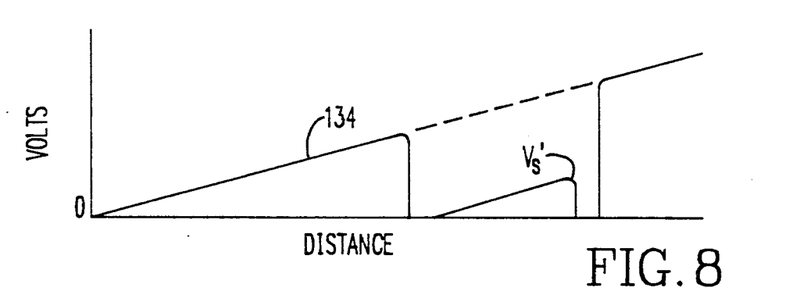

FIG. 8 shows the voltage which would be read on the voltmeter when a cathodic protection current, $i_c$, is flowing. In this case the voltage read, as shown in curve 134, is equal to $i_cR$ as the cylinder is moved along the earth and is zero only at the common connection point of the voltmeter, pipe and test point 24, and under the ring. With the ring removed from contact with the earth, the voltmeter indication would increase along the dashed portion of curve 134. With the ring restored to contact the earth, a shielding effect is obtained and within the halo of influence of the shielding ring, a small $i_cR$ voltage drop, $V'_s$, remains. This small voltage drop generally has the same slope as did the dashed segment and has a magnitude which is related to the inside diameter of the ring. As the inside diameter of the ring is made smaller, the magnitude of $V'_s$ decreases proportionately. A half cell having a diameter of approximately 0.375 inch with a shield of 0.020 inch thickness on a 0.585 inch internal diameter has been demonstrated to have a shielding ratio of about 100:1. That is, the magnitude of $V'_s$ was about one hundredth of the magnitude of the IR drop voltage.

Figure 9:
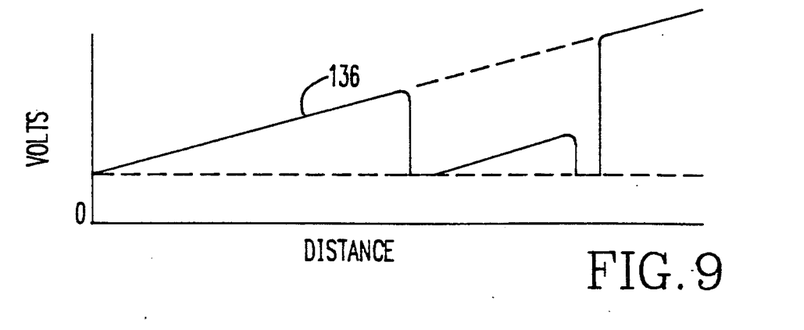

FIG. 9 shows voltages for the case where cathodic current is flowing. As shown by curve 136, for these conditions, an unshielded half cell would indicate voltages of both the half cell electropotential $V_p$ and the IR drop voltage. However, a shielded half cell would indicate voltages of $V_p+V'_s$. The reduction of the error producing IR component is achieved without electronic manipulation of the signals. This provides a convenient, compact, economical, and rugged means for making measurements of cathodic potentials while attenuating the IR voltage drop errors.

Although the invention has been described in terms of its preferred embodiments, it will be apparent to those skilled in the art that various changes may be made without departing from the scope of the invention. For example, while the preferred embodiments were shown as measuring the cathodic protection voltages with respect to underground pipelines, the invention is also applicable to the measurement of cathodic protection voltages on other conductive structures which are in contact with an electrolyte. The operation of the invention does not depend on any special geometry or characteristics of the structure.

What is claimed is:

1. An apparatus for measuring cathodic protection voltage levels on a concealed conductive structure, said apparatus comprising:
    a probe including a standard half cell reference electrode, a working electrode and an auxiliary electrode mounted in a fixed spacial relationship to each other, said reference electrode, working electrode and auxiliary electrode each being in contact with an electrolytic solution;
    a voltage measuring device for receiving a voltage from said reference electrode, said voltage measuring device providing an indication of the voltage difference between said reference electrode and a common reference point;
    means for connecting and disconnecting said working electrode with said common reference point;
    means for detecting voltage between said concealed conductive structure which is subject to a cathodic protection voltage and said common reference point;
    means for providing a bias voltage to said auxiliary electrode in response to a voltage level between said concealed conductive structure and said common reference point; and
    wherein the voltage measured by said voltage measuring device provides an indication of the adequacy of cathodic protection voltage levels on said concealed conductive structure.

2. An apparatus for measuring cathodic protection voltage levels on a concealed conductive structure, as recited in claim 1, wherein:
    said working electrode includes a Luggin capillary connecting two portions of said electrolytic solution on opposite sides of said working electrode.

3. An apparatus for measuring cathodic protection voltage levels on a concealed conductive structure, as recited in claim 1, further comprising:
    an inner tube containing said reference electrode, supporting said working electrode at one end thereof, and supporting said auxiliary electrode on an exterior surface thereof; and
    an outer tube mounted concentrically with said inner tube, said electrolytic solution being contained within said inner and outer tubes.

4. An apparatus for measuring cathodic protection voltage levels on a concealed conductive structure, as recited in claim 1, wherein:
    said reference electrode comprises a silver chloride half cell.

5. An apparatus for measuring cathodic protection voltage levels on a concealed conductive structure, as recited in claim 1, wherein:
    said working electrode has an electropotential substantially equal to that of said concealed structure.

6. A method for measuring cathodic protection voltage levels on a concealed conductive structure, said method comprising the steps of:
    detecting voltage levels by way of a probe including a standard half cell reference electrode, a working electrode and an auxiliary electrode mounted in a fixed spacial relationship to each other, said reference electrode, working electrode and auxiliary electrode each being in contact with an electrolytic solution;
    connecting said working electrode with a common reference point;
    detecting voltage between said concealed conductive structure which is subject to a cathodic protection voltage and said common reference point;
    providing a bias voltage to said auxiliary electrode in response to a voltage level between said concealed conductive structure and said common reference point; and
    measuring the voltage difference between said reference electrode and said common reference point, wherein the voltage difference between said reference electrode and said common reference point provides an indication of the adequacy of cathodic protection voltage levels on said concealed conductive structure.

7. An apparatus for measuring cathodic protection voltage levels on a concealed conductive structure, said apparatus comprising:
    a probe including a standard half cell reference electrode and a metallic electrode mounted in a fixed spacial relationship to each other;
    a voltage measuring device having first input terminal for receiving a voltage from said reference electrode and a second input terminal for connection to a concealed conductive structure which is subject to a cathodic protection voltage;
    a voltage divider electrically connected between said reference electrode and said metallic electrode, said voltage divider including the series connection of first and second resistors;
    switching means for alternatively connecting said reference electrode to said second terminal while disconnecting said metallic electrode from said first input terminal, or connecting said second terminal to a junction point between said first and second resistors while connecting said metallic electrode to said first input terminal.

8. An apparatus for measuring cathodic protection voltage levels on a concealed conductive structure, as recited in claim 7, further comprising:

means for varying the resistance of said first resistor.

9. An apparatus for measuring cathodic protection voltage levels on a concealed conductive structure, as recited in claim 7, further comprising:

a low pass filter connected between said switching means and said first and second input terminals of said voltage measuring device.

10. An apparatus for measuring cathodic protection voltage levels on a concealed conductive structure, as recited in claim 7, wherein:

said reference electrode is generally cylindrical and said metallic electric electrode is a ring mounted concentrically with said reference electrode, said reference electrode and said metallic electrode having coplanar ends.

11. An apparatus for measuring cathodic protection voltage levels on a concealed conductive structure, as recited in claim 7, wherein:

said reference electrode is a copper/copper sulfate electrode; and said metallic electrode has an electropotential equal to or greater than that of the concealed conductive structure.

* * * * *